United States Patent [19]

Ikegami et al.

[11] 4,420,616

[45] Dec. 13, 1983

[54] OXIDATIVE PROCESS FOR THE PREPARATION OF COPPER QUINOLINATE

[75] Inventors: Seishi Ikegami, Yao; Yoshihiro Hatano, Osaka, both of Japan

[73] Assignee: Yamamoto Kagaku Gosei Co., Ltd., Osaka, Japan

[21] Appl. No.: 236,945

[22] Filed: Feb. 20, 1981

[30] Foreign Application Priority Data

Feb. 25, 1980 [JP] Japan .................................. 55-21623

[51] Int. Cl.³ .......................................... C07D 213/87
[52] U.S. Cl. ........................................ 546/5; 546/321
[58] Field of Search ............................................ 546/5

[56] References Cited

U.S. PATENT DOCUMENTS 2,371,691  3/1945  Hankinson .............................. 546/5
4,316,026  2/1982  Hatano et al. ........................... 546/5

OTHER PUBLICATIONS

Stix et al., *Chem. Ber.* 65, p11 (1932).

*Primary Examiner*—Mark L. Berch
*Attorney, Agent, or Firm*—E. Frank McKinney; Paul S. Phillips, Jr.

[57] ABSTRACT

A process for the preparation of copper quinolinate in which quinoline is oxidized by hydrogen peroxide in sulfuric acid in the presence of copper sulfate wherein the reaction is carried out at a pressure of less than 400 mm Hg. The reduced pressure enables the reaction to be performed at higher temperatures and with greater control; also the reaction time is shortened and the yield improved.

Copper quinolinate is used to prepare quinolinic acid which is the starting material for some chromogenic materials used in the pressure-sensitive record material field.

3 Claims, No Drawings

OXIDATIVE PROCESS FOR THE PREPARATION OF COPPER QUINOLINATE

This invention relates to a process for the preparation of copper quinolinate.

Quinolinic aid is assuming increasing importance in the pressure-sensitive record material art where it is needed as a starting material for the synthesis of some chromogenic materials, such as the chromogenic pyridinone materials disclosed in U.S. Pat. No. 3,775,424 which is hereby incorporated by reference. Quinolinic acid is readily prepared from copper quinolinate by reaction with hydrogen sulfide or sodium hydroxide but the preparation of copper quinolinate itself leaves considerable scope for improvement.

Copper quinolinate has hitherto been obtaind by the process described by Stix and Bulgatsch in *Chem. Ber.*, 1932, 65, 11, hereinafter referred to as the Stix process, and comprises the oxidation of quinoline with hydrogen peroxide in sulfuric acid in the presence of copper sulfate. However, at elevated temperatures the oxidation reaction is violently exothermic and difficult to control even with constant cooling of the reaction vessel. Moreover, as the reaction is scaled up, the temperature distribution within the vessel becomes increasingly uneven requiring large and cumbersome cooling apparatus.

Better control of the reaction can of course be achieved by carrying it out at lower temperatures but then the rate of reaction becomes slow resulting in an increased reaction time and in a greater risk of the occurrence of side reactions, such as the decomposition of hydrogen peroxide. Such side reactions will lead in turn to a drop in the yield of copper quinolinate and also to a reduction in its purity. A slow rate of reaction therefore is economically undesirable.

Further disadvantages of the Stix process include the fact that it does not give reproducible yields-on repetition a yield of only 44.7% was obtained-and that the resulting reaction media left after isolation of copper quinolinate is not suitable for re-use in a subsequent run of the process, leading to problems with recovery or waste disposal of the materials present, in particular sulfuric acid and a large amount of copper ions. The Stix process is not therefore suitable for the preparation of copper quinolinate cheaply on an industrial scale.

A considerable improvement in the Stix process was achieved by the process described and claimed in co-pending U.S. patent application Ser. No. 177,694, filed Aug. 12, 1980, now U.S. Pat. No. 4,316,026, which is hereby incorporated by reference. The use of the particular reaction conditions in the improved process afforded a much greater control of the reaction and a much higher yield and purity of copper quinolinate. In addition, the resulting reaction media left after isolation of copper quinolinate can be repeatedly used in subsequent process runs. As increases yields are obtained on repetition and as any unutilized material present in the media is recycled, the process can thus be carried out even more cheaply. And also the repeated use of the media considerably minimizes the problems normally associated with waste disposal of sulfuric acid and copper ions.

It has now been found that an even further improvement in the Stix process can be obtained if it is carried out under a pressure of less than 400 mm Hg. In particular a much greater control of the reaction can be achieved especially at elevated temperatures. But also there are improvements in the yield and purity of copper quinolinate and in the number of repeated uses of the reaction media. These improvements moreover become more significant on scaling up the reaction to an industrial level.

The present invention therefore provides a process for the preparation of copper quinolinate by oxidizing quinoline with hydrogen peroxide in sulfuric acid in the presence of copper sulfate and isolating copper quinolinate from the reaction media, wherein the oxidation reaction is carried out under a pressure of less than 400 mm Hg.

A minimum pressure is not critical to the performance of the invention; all that is required is that the pressure be less than that specified above.

The temperature at which the oxidation reaction is carried out is preferably from 55° to 75° C. and, because of the control over the reaction which can now be achieved by the present invention, it is optimally carried out from 70° to 75° C.

Criticality is attached to the relative amounts and concentrations of the various reactants and it is much preferred to use those amounts and concentrations which are set forth in U.S. application Ser. No. 177,694.

A particular advantage of the present invention is that the resulting reaction media left after isolation of copper quinolinate can be used in a subsequent process run, and, in fact can be so used at least twenty times without any significant variation in yield. Conveniently, the reaction media is concentrated during the course of the reaction as a consequence of it being carried out under a pressure of less than 400 mm Hg. Unlike the process of the U.S. application Ser. No. 177,694, there is therefore no need for an additional step of concentrating the reaction media prior to its re-use in a subsequent process run. The present invention therefore affords a more efficient route to the large scale production of copper quinolinate.

Copper quinolinate can exist in two forms-2:1 copper quinolinate (formula (I)) in which two molecules of quinolinic acid are combined with one atom of copper, and 1:1 copper quinolinate (formula (II)) in which one molecule of quinolinic acid is combined with one atom of copper.

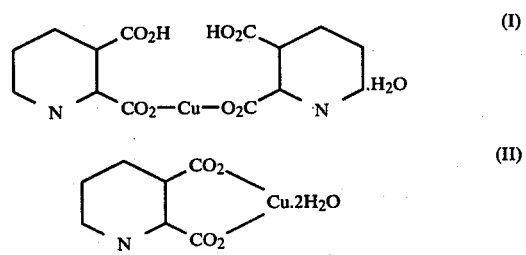

Both of these forms can be prepared by the present process depending on the molar ration of copper sulfate to quinoline. If the ratio is less than or equal to 0.5, the 2:1 copper quinolinate (I) is formed, whereas, if the ratio is greater than 0.5, then the 1:1 copper quinolinate (II) is formed. However, the 2:1 copper salt (I) is preferred since less copper is employed.

The present invention will now be described in more detail with reference to a number of examples, in which all parts are by weight.

EXAMPLE 1

Preparation of 2:1 copper quinolinate under a pressure of 150–400 mm Hg 260 parts of water, 60 parts of concentrated sulfuric acid, 8.0 parts of copper oxide, 25.8 parts of quinoline, and 122.4 parts of 60% hydrogen peroxide were heated to 70° C. Then, under a pressure of 150–400 mm Hg, the reaction was carried out at 70°–75° C. for 4 hours. After cooling, the precipitated 2:1 copper quinolinate was filtered, washed with 100 parts of water, and dried to give 27.3 parts of copper quinolinate (yield, 66.0%). During the course of the reaction, the reaction media had been concentrated to about 250 parts.

EXAMPLE 2

Preparation of 2:1 copper quinolinate by repeated use of reaction media

To the filtrate and washings from example 1 were added 5.6 parts of copper oxide (equivalent to the 2:1 copper quinolinate obtained according to example 1), 25.8 parts of quinoline, and 122.4 parts of 60% hydrogen peroxide, and the temperature was increased to 70° C. Then, under a pressure of 150–400 mm Hg, the reaction was carried out at 70°–75° C. for 4 hours. After cooling, the precipitated 2:1 copper quinolinate was filtered, washed with 100 parts of water, and dried to give 30.9 parts of copper quinolinate (yield, 74.7%). During the course of the reaction, the reaction media had been concentrated to about 250 parts.

The reaction was then repeated a further 18 times except with a slight variation each time in the amount of copper oxide. The results are given in Table 1.

TABLE 1

| Reaction | Reaction media | Copper oxide added (parts) | 2:1 Copper quinolinate Yield (parts) | 2:1 Copper quinolinate Yield (%) |
|---|---|---|---|---|
| 1st | Water 260 parts + conc. sulfuric acid 60 parts | 8.0 | 27.3 | 66.0 |
| 2nd | Filtrate & washing from reaction of the 1st | 5.6 | 30.9 | 74.7 |
| 3rd | Filtrate & washing from reaction of the 2nd | 6.3 | 31.4 | 75.9 |
| 4th | Filtrate & washing from reaction of the 3rd | 6.4 | 32.4 | 78.4 |
| 5th | Filtrate & washing from reaction of the 4th | 6.6 | 31.3 | 75.7 |
| 6th | Filtrate & washing from reaction of the 5th | 6.4 | 32.9 | 79.6 |
| 7th | Filtrate & washing from reaction of the 6th | 6.7 | 31.9 | 77.2 |
| 8th | Filtrate & washing from reaction of the 7th | 6.5 | 32.2 | 77.9 |
| 9th | Filtrate & washing from reaction of the 8th | 6.6 | 32.4 | 78.4 |
| 10th | Filtrate & washing from reaction of the 9th | 6.6 | 32.1 | 77.6 |
| 11th | Filtrate & washing from reaction of the 10th | 6.2 | 32.4 | 78.4 |
| 12th | Filtrate & washing from reaction of the 11th | 6.2 | 31.5 | 76.2 |
| 13th | Filtrate & washing from reaction of the 12th | 6.1 | 32.7 | 79.1 |
| 14th | Filtrate & washing from reaction of the 13th | 6.3 | 31.3 | 75.7 |
| 15th | Filtrate & washing from reaction of the 14th | 6.0 | 31.4 | 75.9 |
| 16th | Filtrate & washing from reaction of the 15th | 6.0 | 32.3 | 78.1 |
| 17th | Filtrate & washing from reaction of the 16th | 6.2 | 32.0 | 77.4 |
| 18th | Filtrate & washing from reaction of the 17th | 6.2 | 31.5 | 76.2 |
| 19th | Filtrate & washing from reaction of the 18th | 6.1 | 31.0 | 75.0 |
| 20th | Filtrate & washing from reaction of the 19th | 6.0 | 30.4 | 73.5 |

It was noticeable that each time the reaction was carried out, its control was very easy. Also, from the foregoing results, it can be seen that substantially high yields of copper quinolinate were constantly obtained.

EXAMPLE 3

Preparation of copper quinolinate by the Stix process (Chem. Ber., 1932, 65, 11)

24 g of quinoline, 2100 ml of 3% hydrogen peroxide, and 46 g of 25% sulfuric acid were heated to 60° C. and 64 g of crystalline copper sulfate dissolved in 160 ml of water were added thereto. As the temperature began to rise after a few minutes, the system was strongly cooled with ice water so as to maintain the temperature below 70° C. However the control of the temperature was extremely difficult, and after the violent exothermic reaction subsided, the reaction was continued for 8 hours at 65°–70° C. Then 200 ml of 3% hydrogen peroxide were added and the reaction was continued for a further 3 hours at 65°–70° C. After cooling, the precipitated copper quinolinate was filtered, washed with water, and dried, giving 22 g of product in a yield of 44.7%. The copper quinolinate obtained was greenish black and low in purity.

Also, the resulting reaction media left after filtration of the copper quinolinate was dark brown, and its re-use as the reaction media was most undesirable as the purity and the yield of the resulting product would seriously suffer and an uncontrollable reaction would tend to occur.

EXAMPLE 4

Preparation of 2:1 copper quinolinate under atmospheric pressure 180 parts of water, 60 parts of concentrated sulfuric acid, 8.0 parts of copper oxide, 25.8 parts of quinoline, and 122.4 parts of 60% hydrogen peroxide were heated to 60° C. Then the reaction was carried out at 60°–70° C. for 5 hours. After cooling, the precipitated 2:1 copper quiniliniate was filtered, washed with 100 parts of water, and dried to give 27.0 parts of the product (yield, 65.3%).

EXAMPLE 5

Preparation of 2:1 copper quinolinate by repeated use of reaction media

After the filtrate and the washings from example 4 had been concentrated to about 230 parts, 5.2 parts of copper oxide, 25.8 parts of quinoline, and 122.4 parts of 60% hydrogen peroxide were added. Then, the reaction was carried out at 60°–70° C. for 5 hours. After cooling, the precipitated 2:1 copper quinolinate was filtered, washed with 100 parts of water, and dried to give 30.0 parts of the product (yield, 72.6%).

The reaction was then repeated a further 10 times except with a slight variation each time in the amount of copper oxide-the results are given in Table 2.

TABLE 2

| Reaction | Reaction media | Copper oxide added (parts) | 2:1 Copper quinolinate Yield (parts) | 2:1 Copper quinolinate Yield (%) |
|---|---|---|---|---|
| 1st | Water 180 parts + conc. sulfuric acid 60 parts | 8.0 | 27.0 | 65.3 |
| 2nd | Filtrate & washings from reaction of the 1st* | 5.2 | 30.0 | 72.6 |
| 3rd | Filtrate & washings from reaction of the 2nd | 5.8 | 31.2 | 75.5 |
| 4th | Filtrate & washings from reaction of the 3rd | 6.0 | 32.3 | 78.1 |
| 5th | Filtrate & washings from reaction of the 4th | 6.2 | 32.7 | 79.1 |
| 6th | Filtrate & washings from reaction of the 5th | 6.3 | 32.0 | 77.4 |
| 7th | Filtrate & washings from reaction of the 6th | 6.2 | 31.9 | 77.1 |
| 8th | Filtrate & washings from reaction of the 7th | 6.1 | 32.0 | 77.4 |
| 9th | Filtrate & washings from reaction of the 8th | 6.2 | 31.3 | 75.7 |
| 10th | Filtrate & washings from reaction of the 9th | 6.0 | 31.0 | 75.0 |
| 11th | Filtrate & washings from reaction of the 10th | 6.0 | 29.9 | 72.3 |
| 12th | Filtrate & washings from reaction of the 11th | 5.7 | 29.5 | 71.3 |

Note:
*Concentrated to about 230 parts before use.

The reactions of examples 4 and 5 required in excess of twice the amount of external cooling water than in the reactions of examples 1 and 2 in spite of the fact that the reaction temperature in the former examples was lower. Moreover control over the reaction was difficult at times in examples 4 and 5 whereas no such difficulty occurred in examples 1 and 2. Further, the yield dropped after the eleventh re-use of the reaction media. As it was expected that a further re-use of the reaction media would result in an additional drop in yield, no further reaction was carried out after the 12th reaction.

EXAMPLE 6

Preparation of quinolinic acid 20.7 parts each of copper quinolinate samples obtained according to Examples 1 and 2 and Examples 4 and 5 were dispersed in 500 parts of water with stirring. Hydrogen sulfide was passed into the dispersion at 60° C. until the blue-coloured copper quinolinate entirely disappeared and a black precipitate of copper sulfide had fully formed. Then, after the copper sulfide had been filtered off, the filtrate was concentrated to give pale yellow quinolinic acid.

The results are shown in Table 3.

TABLE 3

| | 2:1 Copper quinolinate Mean yield (%) | Quinolinic acid Yield (parts) | Quinolinic acid Yield (%) | Overall yield (%)* |
|---|---|---|---|---|
| Examples 1 and 2 Reactions 1st–10th | 76.1 | 14.7 | 87.9 | 66.9 |
| Examples 1 and 2 Reactions 11th–20th | 76.6 | 14.3 | 85.5 | 65.5 |
| Examples 4 and 5 Reactions 1st–10th | 75.3 | 14.4 | 86.1 | 64.8 |

Note:
*Yield based on quinoline.

The 2:1 copper quinolinate obtained in Examples 1 and 2 (reactions 1st–10th) is superior to that obtained in Examples 4 and 5 (reactions 1st–10th) in quality and yield. The 2:1 copper quinolinate obtained in Examples 1 and 2 (reactions 11th–20th) is of somewhat inferior quality, but because of high yield its overall yield is higher than that obtained in Examples 4 and 5 (reactions 1st–10th).

The invention being thus described, it will be obvious that the same may be varied in many ways. Such variations are not to be regarded as a departure from the spirit and scope of the invention, and all such modifications are intended to be included within the scope of the following claims.

We claim:

1. A process for the preparation of copper quinolinate by oxidizing quinoline with hydrogen peroxide in a mixture of water and sulfuric acid in the presence of copper sulfate at a temperature of 55°–75° C. and isolating copper quinolinate from the reaction media, wherein the molar ratio of sulfuric acid to quinoline is greater than 1 to 1, the molar ratio of hydrogen peroxide to quinoline is 10.8 to 1 or greater, the concentration of sulfuric acid is from about 10 to about 30% in said mixture, the oxidation reaction is carried out under a pressure of less than 400 mm Hg and said process is performed by adding copper oxide, quinoline and hydrogen peroxide to the reaction media left after isolation of copper quinolinate prepared according to a previous run of the process.

2. A process according to claim 1, wherein the temperature of the oxidation reaction is from 70°–75° C.

3. A process according to claim 1 or 2, wherein the amount of copper sulfate present in the media is supplemented by an amount equivalent to the amount of copper quinolinate prepared in the previous run and the concentration of sulfuric acid present in the media is adjusted to within the range of 10 to 30%.

* * * * *

UNITED STATES PATENT AND TRADEMARK OFFICE
CERTIFICATE OF CORRECTION

PATENT NO. : 4,420,616

DATED : December 13, 1983

INVENTOR(S) : Seishi Ikegami et al.

It is certified that error appears in the above-identified patent and that said Letters Patent is hereby corrected as shown below:

Column 2, line 50, formula (I), should appear as shown below:

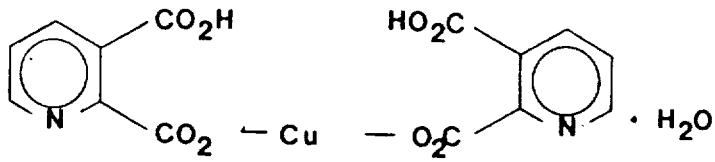

Column 2, line 55, formula (II), should appear as shown below:

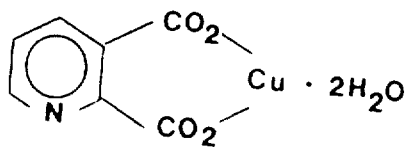

Signed and Sealed this

Twenty-seventh Day of March 1984

[SEAL]

Attest:

GERALD J. MOSSINGHOFF

Attesting Officer     Commissioner of Patents and Trademarks